US009655975B2

(12) United States Patent
Nagasaki et al.

(10) Patent No.: US 9,655,975 B2
(45) Date of Patent: May 23, 2017

(54) PRODRUG USING NITROIMIDAZOLE

(71) Applicant: UNIVERSITY OF TSUKUBA, Ibaraki (JP)

(72) Inventors: Yukio Nagasaki, Ibaraki (JP); Yutaka Ikeda, Ibaraki (JP); Hikaru Hisano, Ibaraki (JP)

(73) Assignee: UNIVERSITY OF TSUKUBA, Ibaraki (JP)

( * ) Notice: Subject to any disclaimer, the term of this patent is extended or adjusted under 35 U.S.C. 154(b) by 154 days.

(21) Appl. No.: 14/376,459

(22) PCT Filed: Feb. 13, 2013

(86) PCT No.: PCT/JP2013/053429
§ 371 (c)(1),
(2) Date: Aug. 4, 2014

(87) PCT Pub. No.: WO2013/122112
PCT Pub. Date: Aug. 22, 2013

(65) Prior Publication Data
US 2014/0378673 A1 Dec. 25, 2014

(30) Foreign Application Priority Data
Feb. 13, 2012 (JP) ................. 2012-028761

(51) Int. Cl.
| A61K 47/46 | (2006.01) |
| A61K 47/48 | (2006.01) |
| C07D 233/91 | (2006.01) |
| C07D 403/06 | (2006.01) |
| C07H 15/252 | (2006.01) |
| C07D 475/08 | (2006.01) |
| C07H 15/244 | (2006.01) |
| C07H 19/06 | (2006.01) |
| A61K 31/196 | (2006.01) |
| A61K 31/198 | (2006.01) |
| A61K 31/519 | (2006.01) |
| A61K 31/58 | (2006.01) |
| A61K 31/704 | (2006.01) |
| A61K 31/7068 | (2006.01) |
| C07H 15/24 | (2006.01) |
| C07D 487/04 | (2006.01) |
| C07J 43/00 | (2006.01) |

(52) U.S. Cl.
CPC ...... *A61K 47/48061* (2013.01); *A61K 31/196* (2013.01); *A61K 31/198* (2013.01); *A61K 31/519* (2013.01); *A61K 31/58* (2013.01); *A61K 31/704* (2013.01); *A61K 31/7068* (2013.01); *C07D 233/91* (2013.01); *C07D 403/06* (2013.01); *C07D 475/08* (2013.01); *C07D 487/04* (2013.01); *C07H 15/24* (2013.01); *C07H 15/244* (2013.01); *C07H 15/252* (2013.01); *C07H 19/06* (2013.01); *C07J 43/003* (2013.01)

(58) Field of Classification Search
None
See application file for complete search history.

(56) References Cited

U.S. PATENT DOCUMENTS

| 3,505,349 A | 4/1970 | Beaman et al. |
| 3,679,698 A | 7/1972 | Beaman et al. |

FOREIGN PATENT DOCUMENTS

| JP | 4-066575 | 3/1992 |
| JP | 7-101860 | 4/1995 |
| WO | 00/64864 | 11/2000 |
| WO | 2004/087075 | 10/2004 |
| WO | 2009/018163 | 2/2009 |

OTHER PUBLICATIONS

International Search Report issued May 21, 2013 in International (PCT) Application No. PCT/JP2013/053429.
L. Kumar et al., "Imidazole Derivatives as Possible Microbicides with Dual Protection", European Journal of Medicinal Chemistry, vol. 45, No. 2, pp. 817-824, 2010.
P. D. Bonnitcha et al., "Nitroimidazole Conjugates of bis(thiosemicarbazonato)$^{64}$Cu(II)—Potential Combination Agents for the PET Imaging of Hypoxia", Journal of Inorganic Biochemistry, vol. 104, No. 2, pp. 126-135, 2010.
Z. Li et al., "Synthesis and In Vitro and In Vivo Evaluation of Three Radioiodinated Nitroimidazole Analogues as Tumor Hypoxia Markers", Nuclear Medicine and Biology, vol. 32, No. 3, pp. 225-231, 2005.
M. P. Hay et al., "Hypoxia-Selective Antitumor Agents. 8. Bis(nitroimidazolyl)alkanecarboxamides: A New Class of Hypoxia-Selective Cytoxins and Hypoxic Cell Radiosensitizers", Journal of Medicinal Chemistry, vol. 37, No. 3, pp. 381-391, 1994.
M. P. Hay et al., "Nitroimidazole-Based 'Extruded Mustards' Designed as Reductively Activated Hypoxia-Selective Cytotoxins", Anti-Cancer Drug Design, vol. 11, No. 5, pp. 383-402, 1996.
L. Mei et al., "$^{99m}$Tc/Re Complexes Bearing Bisnitroimidazole or Mononitroimidazole as Potential Bioreductive Markers for Tumor: Synthesis, Physicochemical Characterization and Biological Evaluation", European Journal of Medicinal Chemistry, vol. 58, pp. 50-63, 2012.
B. M. Sykes et al., "*N*Substituted 2-(2,6-Dinitrophenylamino)Propanamides: Novel Prodrugs that Release a Primary Amine via Nitroreduction and Intramolecular Cyclization", J. Med. Chem., vol. 42, pp. 346-355, 1999.
J. X. Duan et al., "Potent and Highly Selective Hypoxia-Activated Achiral Phosphoramide Mustards as Anticancer Drugs", J. Med. Chem., vol. 51, pp. 2412-2420, 2008.
Extended European Search Report issued Aug. 6, 2015 in corresponding European patent application No. 13 74 8732.
Anonymous: "Nitrogen mustard—Wikipedia, the free encyclopedia", Jan. 29, 2012, XP055203594.

*Primary Examiner* — Shaojia Anna Jiang
*Assistant Examiner* — Dale R Miller
(74) *Attorney, Agent, or Firm* — Wenderoth, Lind & Ponack, L.L.P.

(57) ABSTRACT

Provided is a prodrug of 2-nitro-1-imidazolepropionic acid and a therapeutically active organic compound having on the molecule an amino group, a cyclic amino group or a hydroxyl group, particularly a prodrug in which the therapeutically active organic compound is selected from among antitumor agents. The prodrug cleaves specifically under hypoxic conditions in vivo to exhibit the inherent therapeutic activity.

4 Claims, 4 Drawing Sheets

PRODRUG USING NITROIMIDAZOLE

TECHNICAL FIELD

This invention relates to a conjugate of 2-nitro-1-imidazolepropionic acid and a drug that is a therapeutically active compound. More specifically, the invention relates to such a prodrug in which a covalent bond between nitroimidazole and the drug cleaves at a hypoxic region in a living organism or in a reducing environment, enabling a therapeutically active compound to be released in an active form, and to the use of 2-nitro-1-imidazolepropionic acid for providing such a conjugate.

BACKGROUND ART

Tumors at hypoxic regions cause invasive, metastatic and chemoresistant cancers, and are the biggest factor preventing a complete cure of cancer. There is an urgent desire for the development of methods for treating tumor cells in such low-oxygen environments.

Several kinds of clinical trials are currently being conducted on the following and other drugs targeted at cancer cells in hypoxic regions: triapazamine, AQ4N (banoxantrone dihydrochloride), PR104 (dinitrobenzamide nitrogen mustard prodrug) and TH-302 (N,N'-bis(2-bromoethyl) phosphorodiamidic acid (1-methyl-2-nitro-1H-imidazol-5-yl) methyl ester. However, at present, there is no information to indicate that these have been brought to market.

Dinitrobenzamide and other compounds which act as such protecting groups are disclosed in Non-Patent Document 1 and nitroimidazoles relating to TH-302 are disclosed in Non-Patent Document 2, Patent Document 1 and Patent Document 2. TH-302, as shown in the following reaction scheme, is understood to utilize the mechanism of cleaving the protecting group-drug bond to release the drug.

[Chemical formula 1]

In both Patent Documents 1 and 2, the drug is bonded through a methyleneoxy group (—CH$_2$—O—) to a carbon atom on the imidazole ring, and is understood to be released from the prodrug by the same mechanism as in the above reaction scheme. However, in this system, the efficiency of drug release is dependent on the leaving ability of the drug; the drug that is released is limited to a compound having a phenolic hydroxyl group or phosphoric acid that readily dissociates.

Patent Document 3 mentions a hypoxia-activated conjugate (Hyp-L-Q) obtained by covalently bonding a bioreductive group (Hyp: e.g., 2-nitroimidazolyl) at the 1 position thereon through a linker (L: —CH$_2$CH$_2$CH$_2$—C(=O)—) to the amino group on an anthracycline-based anticancer agent (Q). With regard to this compound which is a conjugate, in a hypoxic tumor region, although the -L-Q moiety remained bonded, the nitro group on 2-nitroimidazolyl is reduced to hydroxyamine, which suggests that DNA can be alkylated through the 4- or 5-position on imidazolyl and that, at the same time, the anthracycline making up Q is intercalated between DNA bases, thereby killing cancer cells. However, it was revealed in this patent publication that a compound in which the linker is "—C3H6-C(=O)—", as compared with a corresponding compound in which the linker is —CH$_2$ (CH$_2$)$_a$CH$_2$—O—CH$_2$— ("a" here being the integer 0 or 1), for example, exhibits only a very low cytotoxicity to lung cancer cells under hypoxic conditions. Hence, such a compound falls outside the scope of the claims of this patent application.

In addition, Patent Document 4 mentions that amides such as N-methyl-2-nitro-1-imidazole propanoylamide, for example, have a radiation-sensitizing action and also have, by themselves, an anticancer effect. However, no mention or suggestion whatsoever has been made that such imidazole carboxylic acids can be used to form conjugates or prodrugs with other drugs.

CITATION LIST

Patent Literature Document

Patent Document 1: WO 2000/64864 or Japanese Translation of PCT Application No. 2002-543059
Patent Document 2: WO 2004/087075 or Japanese Translation of PCT Application No. 2006-521409
Patent Document 3: WO 2009/018163 A1
Patent Document 4: JP Hei 7-101860 A (1995)

Non-Patent Literature Document

Non-Patent Document 1: B. M Sykes et al., *J. Med. Chem.* 42, 345-355 (1999)
Non-Patent Document 2: J. Duan et al., *J Med. Chem.* 51(8): 2412-2420 (2008)

SUMMARY OF THE INVENTION

Technical Problem

The inventors inferred that, because 2-nitroimidazole has a relatively high redox potential and is efficiently reduced at hypoxic regions in vivo, the nitro group is reduced to hydroxyamine and amine, and that, were it possible to apply the structural change in the molecule which thus arises to the release of a compound, this would lead to the development of carcinostatic drugs specific to hypoxic regions. In other words, if a compound lacks activity at a normal oxygen concentration because it exists in the form of a prodrug, but undergoes a structural change and assumes an active form in hypoxic regions, this should enable the development of a pharmaceutical product which suppresses the side effects of the anticancer drug but is active in hypoxic regions. Accordingly, the object of this invention is to provide a system which is more versatile than the conventional art and in which the molecular structure specifically changes in hypoxic regions such as tumors, efficiently releasing a compound such as a drug.

Solution to Problem

It is implied in Non-Patent Document 1 that, in a compound having a drug covalently bonded to the carbonyl group of the linker —CH(-Me)-C(=O)— which is itself bonded at the 1 position of a 2-nitroimidazole skeleton, an intramolecular cyclization reaction does not arise even when the nitroimidazole moiety is reduced, and so the drug is not released. At the same time, with regard to Hyp-L-Q in which the linker portion is —CH$_2$CH$_2$CH$_2$—C(=O)—, Patent Document 3 mentions that although the 2-nitroimidazole moiety corresponding to Hyp is reduced under hypoxic conditions, the L-Q bond does not cleave.

Surprisingly, the inventors have found that an amide bond, imide bond or ester bond that has been formed through such a carbonyl group cleaves in a reducing environment, especially at hypoxic regions in vivo.

Such cleavage, although not theoretically constrained, can be understood as arising together with an intramolecular cyclization reaction according to the following reaction scheme in which the nitro group on the imidazole ring is converted to a hydroxyamine or amino group in a reducing environment, which amino group carries out intramolecular nucleophilic attack.

[Chemical formula 2]

According to the present invention, there can be provided a compound capable of serving as a conjugate or prodrug for a wide variety of drugs, which compound, because the amide bond, imide bond or ester bond cleaves in a reducing environment, releasing a drug having its own activity at that place, is technically meaningful in that release occurs selectively in a reducing environment.

Hence, this invention is based on the discovery that 2-nitro-1-imidazolepropionic acid can be used to provide a wide variety of drugs, especially prodrugs of therapeutically active organic compounds.

In one aspect, the invention provides a compound represented by general formula (I), or a pharmaceutically acceptable salt thereof,

[Chemical formula 3]

(I)

wherein Z is of formula (a):

[Chemical formula 4]

(a)

or formula (b)

—O—R3 (b).

In these formulas, R1 is a residue of an amino group-bearing therapeutically active organic compound after removal of the amino group therefrom and R2 is a hydrogen atom, or R1 and R2 represent, together with the adjoining nitrogen atom, a residue of a therapeutically active organic compound having a cyclic amino group; and R3 is a residue of a hydroxyl group-bearing therapeutically active organic compound after removal of the hydroxyl group therefrom.

In other aspects, the invention provides a preparation for producing a prodrug of a therapeutically active organic compound which has an amino group, a cyclic amino group or a hydroxyl group on the molecule and includes 2-nitro-1-imidazolepropionic acid of formula (II)

[Chemical formula 5]

(II)

as a reactant; and also provides the use of a compound of formula (II) as a reactant for producing a prodrug of a therapeutically active organic compound having on the molecule an amino group, a cyclic amino group or a hydroxyl group.

In such a compound represented by general formula (I), because 2-nitro-1-imidazolepropionyl (sometimes abbreviated below as "Izp") is bonded to a therapeutically active organic compound, it lowers or masks the biological activity inherent to the organic compound (such as cytotoxicity and other activities), yet the Izp moiety and the moiety corresponding to Z selectively cleave in a reducing environment, particularly in hypoxic regions within mammals. The inherent activity of the organic compound furnished by such cleavage is exhibited at hypoxic regions and the periphery thereof.

Accordingly, the compound represented by general formula (I) is able to release the therapeutically active organic compound included therein at specific regions within a mammal, thereby enabling safer and more effective use.

DETAILED DESCRIPTION OF THE INVENTION

Unless otherwise defined, technical terms used in this specification or used with regard to this invention bear the meaning and import with which they are generally used in the technical field to which this invention pertains.

As used herein, "prodrug" has the meaning with which it is used within this technical field. For example, it refers to a compound which chemically modifies a physiologically active substance or a therapeutically active organic compound and has been designed to dissociate or release the parent compound in vivo under enzymatic or other conditions.

"Conjugate" refers to an entity formed by covalently bonding two or more different compounds, and is used as a concept that encompasses prodrugs.

"Therapeutically active organic compound" refers to an organic compound having a therapeutic or prophylactic activity against diseases, disorders or the like in mammals, particularly humans. Examples of such diseases and disorders include tumors, especially malignant tumors, and inflammation, which lesions or regions peripheral thereto are associated with a hypoxic state compared with normal tissue or cell regions.

"Antitumor drug or substance" and "anticancer drug" are used as interchangeable terms.

Antitumor substances encompassed by therapeutically active organic compounds include not only compounds currently used in cancer chemotherapy or being tested for use, but also compounds whose clinical use has been abandoned on account of strong toxicity or side effects, and compounds which will in the future be provided as anticancer drugs, so long as they suit the purposes of this invention. Such anticancer drugs include, but are not limited to, anthracycline-based compounds such as doxorubicin, idarubicin, epirubicin, daunorubicin, pirarubicin, amrubicin, aclacinomycin, anthramycin and zorubicin; peptide-based compounds such as bleomycin and actinomycin; quinoline alkaloid-based compounds such as camptothecin, topotecan and irinotecan; taxane-based compounds such as docetaxel and paclitaxel; vinca alkaloid-based compounds such as vinorelbine, vincristine, vinblastine and vindesine; deoxycytidine-based compounds such as gemcitabine and cytarabine; pyrimidine-based compounds such as 5-fluorouracil, capecitabine and doxyfluridine; purine ring derivative-based compounds such as fludarabine, 6-mercaptopurine and 6-thioguanine; macrolide-based compounds such as epothilone; amino acid derivative-based compounds such as melphalan; and folic acid derivative-based compounds such as methotrexate and pemetrexed.

Anti-inflammatory substances encompassed by therapeutically active organic compounds include salicylic acid-based non-steroidal anti-inflammatory drugs such as mesalazine; oxicam-type non-steroidal anti-inflammatory drugs such as piroxicam, meloxicam and tenoxicam; and steroidal-based anti-inflammatory drugs such as cortisone, hydrocortisone, cortisone acetate, prednisolone, methylprednisolone, betamethasone, dexamethasone, triamcinolone and triamcinolone acetonide.

Examples of the amino group, cyclic amino group or hydroxyl group which is present within the molecule of these antitumor substances and can be used to form an amide bond, imide bond or ester bond by reaction with the compound of formula (II) include the following: in anthracyclines, an amino group or hydroxyl group present on the sugar moiety; in peptide-based antibiotics, an amino group; in quinoline alkaloids, a hydroxyl group on the E ring; in taxanes, a hydroxyl group bonded to the taxane ring or a side-chain hydroxyl; in vinca alkaloids, a cyclic amino group on the indole ring; in deoxycytidine derivatives, an exocyclic amino group on the cytosine base or a hydroxyl on the ribose ring; in pyrimidine derivatives, a cyclic amino group on the pyrimidine ring or a hydroxyl on the ribose ring; in purine ring derivatives, a cyclic amino group or exocyclic amino group on the purine ring or a hydroxyl group on the ribose ring; in macrolide antibiotics, a hydroxyl group on the macrolide ring; in amino acid derivatives, an amino group bonded to the a carbon; and in folic acid metabolic antagonists, an amino group bonded to the heterocycle.

Examples of the amino group, cyclic amino group or hydroxyl group which is present on the molecule of an anti-inflammatory agent and may be used to form an amide bond, imide bond or ester bond by reacting with the formula (II) compound include the following: in salicylic acid-based compounds, a hydroxyl group or amino group bonded to the benzene ring; in oxicam-based compounds, a hydroxyl group present on the cyclic sulfonamide; and in steroidal compounds, a hydroxyl group bonded to the carbon at position 21.

Therefore, illustrative examples of compounds of general formula (I) which are amino group-bearing therapeutically active organic compounds include doxorubicin, idarubicin, epirubicin, daunorubicin, pirarubicin, amrubicin, aclacinomycin, anthramycin, zorubicin, bleomycin, actinomycin, gemcitabine, cytarabine, methotrexate, pemetrexed, melphalan and mesalazine;

which are cyclic amino group-bearing therapeutically active organic compounds include vincristine, vinblastine, vindesine, 5-fluorouracil and 6-mercaptopurine; and which are hydroxyl group-bearing therapeutically active organic compounds include docetaxel, paclitaxel, vincristine, vinblastine, vindesine, doxorubicin, idarubicin, epirubicin, daunorubicin, pirarubicin, amrubicin, aclacinomycin, anthramycin, zorubicin, bleomycin, actinomycin, gemcitabine, cytarabine, capecitabine, doxyfluridine, epothilone, piroxicam, meloxicam, tenoxicam, cortisone, hydrocortisone, cortisone acetate, prednisolone, methylprednisolone, betamethasone, dexamethasone, triamcinolone and triamcinolone acetonide.

Of these, examples of preferred therapeutically active organic compounds include doxorubicin, idarubicin, epirubicin, daunorubicin, pirarubicin, amrubicin, aclacinomycin, anthramycin, zorubicin, bleomycin, actinomycin, camptothecin, topotecan, irinotecan, docetaxel, paclitaxel, vinorelbine, vincristine, vinblastine, vindesine, gemcitabine, cytarabine, 5-fluorouracil, capecitabine, doxyfluridine, fludarabine, 6-mercaptopurine, 6-thioguanine, epothilone, piroxicam, melphalan, methotrexate, pemetrexed, mesalazine, prednisolone, methylprednisolone, dexamethasone and betamethasone. Especially preferred examples include doxorubicin, idarubicin, epirubicin, daunorubicin, pirarubicin, amrubicin, aclacinomycin, anthramycin, zorubicin, gemcitabine, cytarabine, methotrexate, pemetrexed, melphalan, mesalazine, vincristine, vinblastine, vindesine, 5-fluorouracil, 6-mercaptopurine and prednisolone.

Pharmaceutically acceptable salts of the compound represented by general formula (I), in cases where the compound has a basic group other than the amino group or cyclic amino group that forms an amide bond or imide bond, may be acid addition salts of mineral acids such as hydrochloric acid and sulfuric acid or organic acids such as formic acid, acetic acid, citric acid and methanesulfonic acid. In cases where the compound has an acidic group such as a carboxyl group or a hydroxyl group, pharmaceutically acceptable salts of the compound may be base addition salts of alkali metals such as sodium and potassium, ammonium, or organic amines such as methylamine.

In this invention, "hypoxic region" is used without regard to whether the site is in vivo or in vitro, although this term encompasses in particular solid cancer lesions or solid cancer cell masses, and regions peripheral thereto, preferably in living mammals, and especially humans.

Production of the compound represented by general formula (I) by the reaction of a therapeutically active organic compound having an amino group, a cyclic amino group and/or a hydroxyl group on the molecule with a compound of formula (II) to form an amide bond, an imide bond or an ester bond may be carried out by reacting the organic compound with a compound of formula (II) within a suitable inert solvent and in the presence of a condensing agent (e.g., a carbodiimide) that is itself commonly known in the technical field pertaining to the invention, or by reacting an active ester (e.g., an ester with a halide or N-hydroxysuccinimide) of the compound of formula (II) with the compound represented by general formula (I) in a suitable solvent. When an amino group or cyclic amino group and a hydroxyl group are both present on the molecule of the organic compound, if necessary, one of the above reactions may be carried out after either group has been protected by a method that is familiar within the field of the invention.

The compound or prodrug of general formula (I) may be administered to the patient in the same dosage form and by the same route of administration as the therapeutically active organic compound serving as the parent compound. Although not subject to any particular limitation, the pharmaceutical preparation may be prepared using a pharmaceutically acceptable carrier. For example, pharmaceutical preparations suitable for parenteral or intramuscular administration may be prepared by dissolution or suspension in an aqueous or nonaqueous solution or dilution in which a buffer, a tonicity modifier and the like have been included and which optionally includes, for example, a surfactant, a liposome-forming agent, a polymer micelle-forming agent and the like. The amount administered should be set while referring to the dose of the parent compound and, where necessary, consulting with a specialist.

DESCRIPTION OF THE EMBODIMENTS

The invention is described more concretely below by way of examples, although the examples are not intended to limit the invention.

Example 1

Reduction of Methyl 3-(2-Nitro-1H-Imidazolyl)propionate

Reaction Scheme:

[Chemical formula 6]

Figure 1:
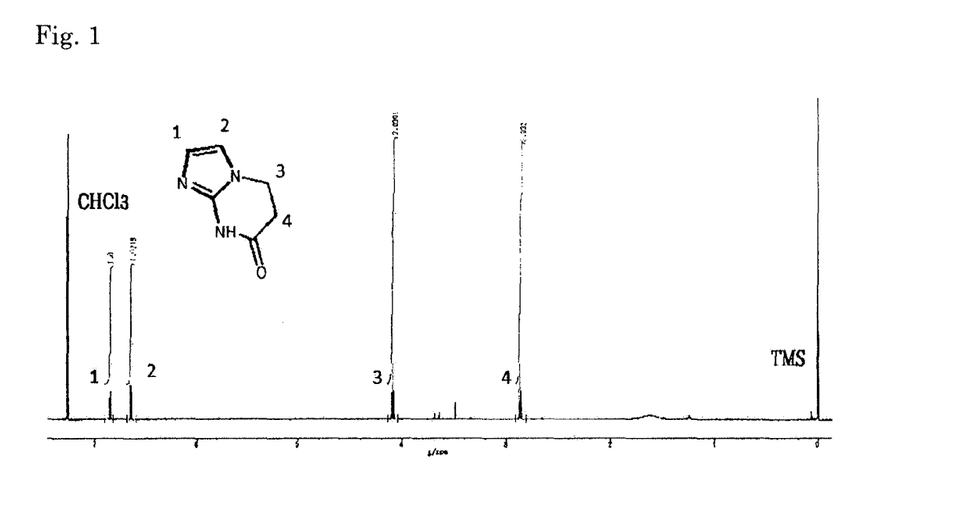
FIG. 1 is an NMR chart of Compound 4 synthesized by a cyclization reaction in Example 1.

A reaction tube to which had been added 200 mg of Compound 1 synthesized according to a method described in the non-patent document (M. P. Hay et al., *J. Med. Chem.* 37, 381-391 (1994)) was charged with 10 mL of methanol and 150 mg of Pd/C, then filled with hydrogen gas. With the tube filled with hydrogen gas, stirring was continued for 24 hours. Following the reaction, thin-layer chromatography (TLC) (developing solvent, ethyl acetate:hexane=1:1) was used to confirm that the reaction had proceeded. Next, the Pd/C was removed by Celite filtration and, last of all, the methanol was removed using an evaporator. As a result, a ring structure was rapidly formed in solution during the reducing reaction, without isolation of the Intermediate 3, yielding Compound 4. FIG. 1 shows an NMR chart of the Compound 4 thus obtained.

It was confirmed from this chart that Compound 4 having a cyclic structure formed due to the reduction of Compound (1). Hence, it is apparent that, together with an intramolecular cyclization reaction by the compound analog of formula (I), the ester bond cleaves, releasing HOMe.

Example 2

Preparation of N-Naphthylmethyl-3-(2-Nitro-1H-Imidazolyl)propionylamide

Reaction Scheme:

[Chemical formula 7]

A 50 mL round-bottomed flask was charged with Compound 2 (100 mg) synthesized according to a method described in the non-patent document (M. P. Hay et al., *J. Med. Chem.* 37, 381-391 (1994)), following which 1-ethyl-3-(3-dimethylaminopropyl)carbodiimide hydrochloride (155.6 mg), N,N-dimethyl-4-aminopyridine (6.7 mg), methylene chloride (5.4 mL) and 1-naphthylmethylamine (119.27 µL) were added to the reactor under stirring with a stirrer and stirring was continued for two days. A 100 mL separatory funnel was charged with 20 mL of ethyl acetate and 20 mL of saturated ammonium chloride, and the organic phase and aqueous phase were separated. A saturated aqueous solution of sodium bicarbonate and a saturated aqueous solution of NaCl were added to the recovered ethyl acetate phase and separation was carried out, thereby recovering the organic phase. The organic phase was dried over anhydrous $Na_2SO_4$, following which the solvent was removed with an evaporator. The residue was isolated and purified by silica gel column chromatography (developing solvent, ethyl acetate:hexane=1:1; 400 mL), and the solvent was removed with an evaporator, yielding the target Compound 5.

ESI-MS (M+H$^+$): theoretical value, 325.130; measured value, 325.126

Example 3

Reduction of Compound 5

A stirring bar and Compound 5 (10 mg) were added to a 50 mL round-bottomed flask. While stirring with the stirrer, 10 mL of methanol and 50 mg of Pd/C were added to the reactor, and the reactor was filled with hydrogen gas. With the reactor filled with hydrogen gas, stirring was continued for 24 hours. Following the reaction, TLC (developing solvent, ethyl acetate:hexane=1:1) was used to confirm that the reaction had proceeded. Next, the Pd/C was removed by Celite filtration and, last of all, the methanol was removed using an evaporator. Analysis by electrospray ionization mass spectroscopy (ESI-MS) yielded results indicating the formation of Compound 4. This showed that, together with an intramolecular cyclization reaction, the amide bond cleaved, releasing naphthylmethylamine.

Compound 4: theoretical molecular weight, 138.067; measured value, 138.063

Example 4

Incubation of Compound 5 in Cultured Cells Under Low Oxygen

This example was carried out to confirm that Compound 5 is reduced in cells within a hypoxic environment, and that naphthylmethylamine is released by a subsequent intramolecular cyclization reaction.

Figure 2:
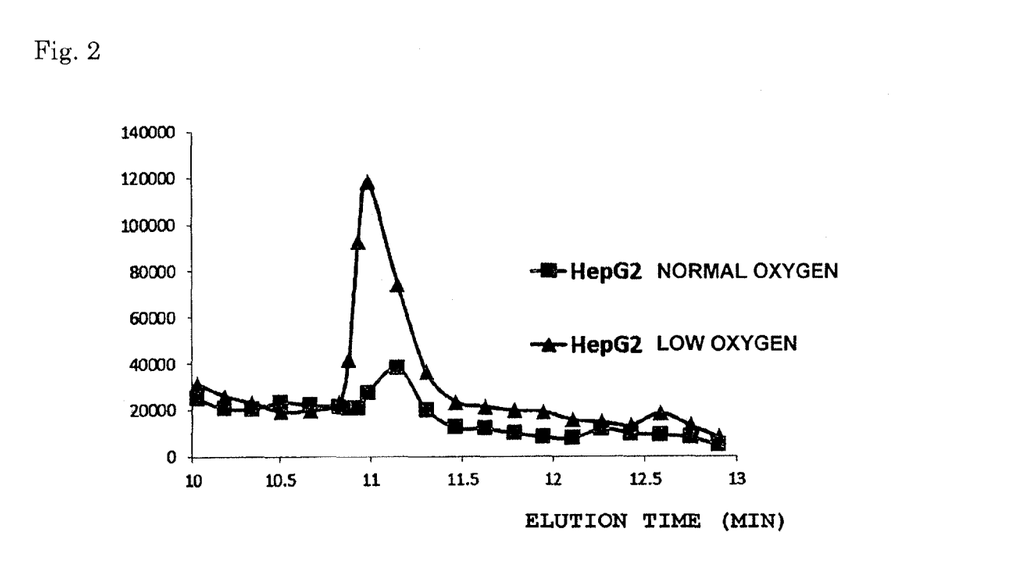
FIG. 2 is a graph showing the results of high-performance liquid chromatography (HPLC) comparing the amount of naphthylmethylamine released in normal oxygen and low-oxygen environments in Example 4.

A cell suspension prepared to a cell count of $1\times10^4$ cells/mL was dispensed into a 96-well plate, and the cells were cultured by 24 hours of incubation at 37° C. After 24 hours, the synthesized Compound 5 was added to the cells in an amount of 1 mM. Following addition, the cells were cultured for 6 hours each in a normal oxygen concentration incubator (20% $O_2$) or at a low-oxygen work station (1% $O_2$). The culture medium was then recovered, 50 µL of Trypsin/EDTA was added and 5 minutes of incubation was carried out, following which the cells were stripped away and added to the medium that was earlier recovered. Next, the recovered sample was freeze-dried overnight, 200 µL of acetonitrile was added, and 30 minutes of ultrasonic cleaning was carried out. In addition, dead cells were precipitated by centrifugal separation (3,000 rpm, 10 min), the supernatant was recovered, and the acetonitrile was removed with a centrifugal evaporator. Next, 200 µL of methanol (for LC/MS) was added to the Eppendorf tube used in centrifugation, the tube contents were passed through a filter (0.2 µm), and LC/MS measurement and high-performance liquid chromatography (HPLC) measurement were carried out. By carrying out this measurement, the amount of compound released in a low-oxygen environment and the amount released in a normal oxygen environment were compared. The HPLC results are shown in FIG. 2. It is apparent from the diagram that much naphthylmethylamine is released in a low-oxygen environment.

Example 5

Incubation of Compound 5 in Cultured Cells Under Low Oxygen

Human pancreatic cancer cells (MIA PaCa-2, acquired from Riken Cell Bank) were prepared as a suspension having a cell count of $1\times10^4$ cells/mL), and dispensed into a 96-well plate. After 24 hours, Compound 5 was added to a concentration of 10 µM and the cells were cultured, in a normal oxygen concentration incubator (20% $O_2$) or at a low-oxygen work station (0.1% $O_2$). After a given time had elapsed, the culture medium was recovered, trypsin was added and the cells were recovered. The recovered cells were disrupted by sonic treatment, the compound was extracted with acetonitrile, and analysis by LC/MS was carried out under the following conditions.

Column used: Lachrom Ultra C18 (particle size, 2 μm; 2 mm×50 mm) column
Measurement wavelength: 220 nm
Eluent A: 0.1% TFA-containing milliQ
Eluent B: acetonitrile
Flow rate: 0.2 mL/min
Gradient: 95:5 (Eluent A:Eluent B)→95:5 (5 minutes)→30:70 (15 minutes)

Figure 3:
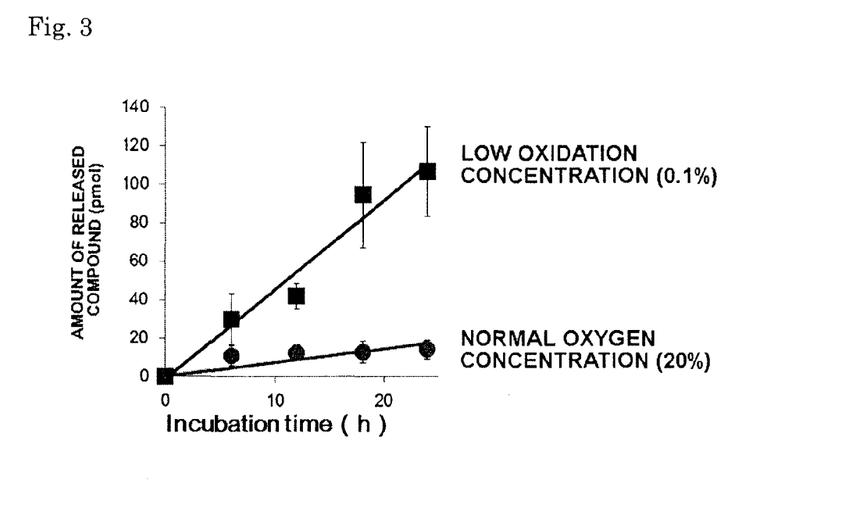
FIG. 3 is a graph showing the release behavior of an amino group-bearing organic compound from a model compound represented by general formula (I) using human pancreatic cancer cells in Example 5.

By carrying out this measurement, the amount of compound released in a low-oxygen environment and the amount of compound released in a normal oxygen environment were compared. The HPLC results are shown in FIG. 3. It is apparent from the diagram than much naphthylmethylamine is released in a low-oxygen environment.

Example 6

Production of Doxorubicin Prodrug

Reaction Scheme:

[Chemical formula 8]

(1) Synthesis of Compound 6

1-Ethyl-3-(3-dimethylaminopropyl)carbodiimide hydrochloride (80.8 mg) was added to Compound 2 (60 mg) synthesized in the same way as in Example 2, following which N-hydroxysuccinimide (48 mg) was added and the reaction was carried out in N,N-dimethylformamide (1 mL) for 1 hour under ice cooling, then for 3 hours at room temperature. Following the reaction, several drops of acetic acid were added dropwise under ice cooling and the system was stirred for 30 minutes. Partitioning between ethyl acetate and saturated saline was carried out, after which the organic phase was concentrated by evaporation. Next, 2-propanol was added and heating was carried out, after which impurities were filtered off and the filtrate was ice-cooled, yielding Compound 6 (50 mg). ESI-MS (M+H$^+$); theoretical value, 283.068; measured value, 283.079

(2) Synthesis of Compound 7

Compound 6 (2.2 mg) was added, within a mixed solvent of N,N-dimethylformamide (50 μL) and water (50 μL), to doxorubicin (3 mg), after which triethylamine (1.4 μL) was added and the reaction was carried out for 24 hours at room temperature. Following the reaction, purification was carried out with a reversed phase HPLC column (GL Sciences Inc.; Inertsil ODS-3, 20×50 mm; flow rate, 5 mL/min; developing solution, methanol/water=60/40 (0 min) to 100/0 (20 min)).

ESI-MS (M+Na$^+$): theoretical value, 733.1967; measured value, 733.2013

Compound 7 in the above reaction scheme was thereby obtained.

Example 7

Evaluation of Cell Survival Rate (Low-Oxygen Environment-Responsive Doxorubicin)

Figure 4:
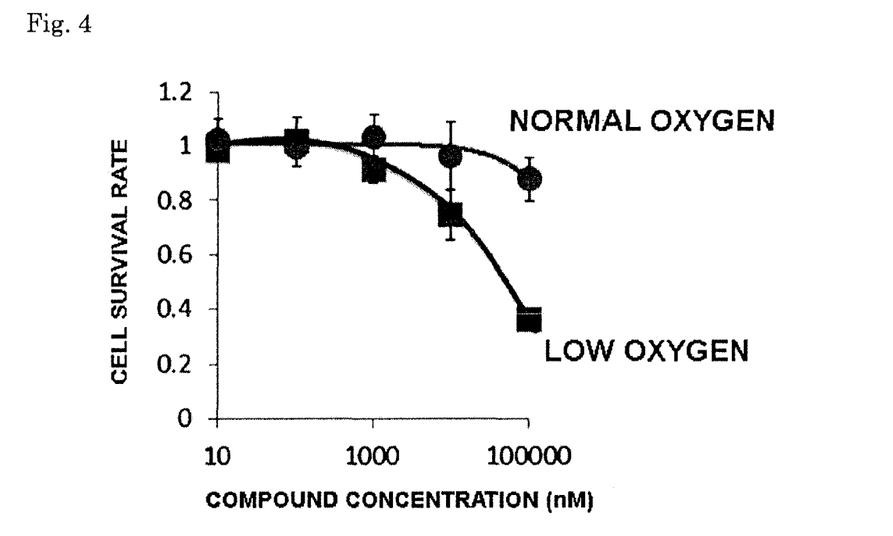
FIG. 4 is a graph showing the results of an evaluation of cell survival rates in Example 7 (hypoxic environment-responsive doxorubicin).

Human pancreatic cancer cells (MIA PaCa-2, acquired from Riken Cell Bank) were dispensed at a density of 5,000 cells/well and cultured for 24 hours in Dulbecco's modified Eagle medium (DMEM), following which Compound 7 was added to the specified concentration and 6 hours of culturing was carried out at a normal oxygen concentration (20%) or a low oxygen concentration (0.1%). After culturing, DMEM medium replacement was carried out, the compound was removed, and 48 hours of culturing was carried out in a normal oxygen concentration incubator, following which the cell survival rate was analyzed by a WST assay. The results are shown in FIG. 4.

It is apparent from the diagram that Compound 7 significantly lowers the survival rate of human pancreatic cancer cells at a low-oxygen concentration compared with a normal oxygen concentration.

Comparative Example

Figure 5:
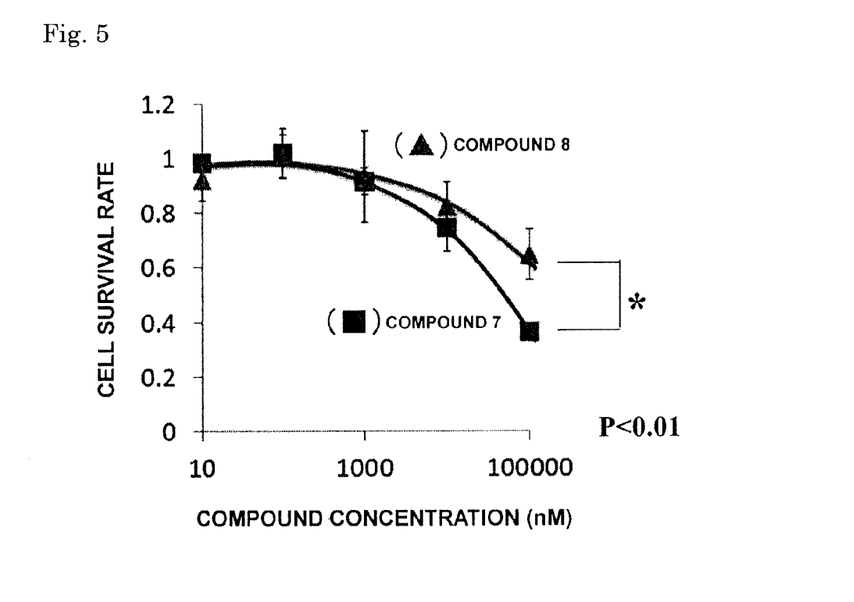
FIG. 5 is a graph showing the results of a comparative test on the cytotoxicity of known compounds that are structurally analogous to the compounds of the invention in a comparative test example.

Comparison of Cytotoxicities of Inventive Compound and a Known Compound that is Structurally Similar Compound 8 below, which is mentioned in WO 2009/018163 A1, was furnished for use. The cell survival rates were compared in tests conducted by the method described in Example 7 on both Compound 8 and a compound within the scope of this invention (aside from the fact that the corresponding linker was —CH$_2$CH$_2$C(=O)—, the manner of bonding between nitroimidazole and the drug was the same; Compound 7 of Example 6). The results are shown in FIG. 5.

[Chemical formula 9]

From the diagram, compared with known Compound 8, Compound 7 according to this invention shows a significantly higher cytotoxicity against human pancreatic cancer cells.

Example 8

Synthesis of Low Oxygen Environment-Responsive Gemcitabine Prodrug

Reaction Scheme :

Compound 6 ⟶

[Chemical formula 10]

Trimethylchlorosilane (47 μL) was added to gemcitabine (22 mg) dissolved in pyridine (1 mL), and stirring was carried out for 2 hours at 0° C. Next, Compound 6 dissolved in acetonitrile (1 mL) was added and stirred for 12 hours at 45° C. The reaction was followed by the addition of ethanol (1 mL) and 30 minutes of stirring at 45° C., then the addition of water (1 mL) and 30 minutes of stirring at 45° C. The solvent was removed by evaporation, followed by purification with a reversed phase HPLC column (GL Sciences Inc.; Inertsil ODS-3, 20×50 mm; flow rate, 5 mL/min; developing solution, acetonitrile/water=20/80 (0 min) to 50/50 (30 min)).

This gave purified Compound 9 in a yield of 20%.

ESI-MS [M+H]$^+$: theoretical value, 431.11; measured value, 431.20

Example 9

Evaluation of Cell Survival Rate (Low-Oxygen Environment-Responsive Gemcitabine)

Figure 6:
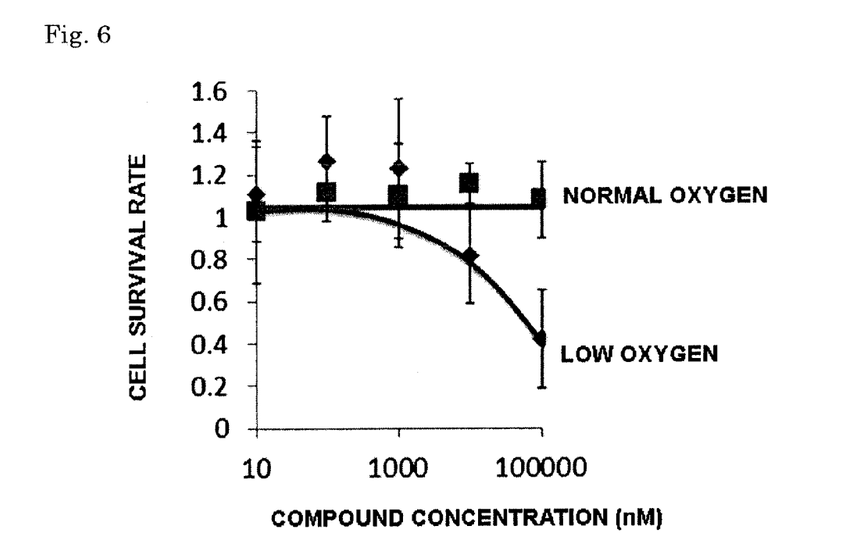
FIG. 6 is a graph showing the results of a cell survival rate evaluation (hypoxic environment-responsive gemcitabine) in Example 9.

Human pancreatic cancer cells (MIA PaCa-2, acquired from Riken Cell Bank) were dispensed at a density of 5,000 cells/well and cultured for 24 hours in DMEM medium, following which Compound 9 was added to the specified concentration and 1 hour of culturing was carried out at a normal oxygen concentration (20%) or a low oxygen concentration (0.1%). After culturing, DMEM medium replacement was carried out, Compound 9 was removed, and 48 hours of culturing was carried out in a normal oxygen concentration incubator, following which the cell survival rate was analyzed by a WST assay. The results are shown in FIG. 6.

Example 10

Synthesis of Low Oxygen Environment-Responsive Fluorouracil Prodrug

Reaction Scheme:

Thionyl chloride (500 μL) was added to Compound 2 (30 mg) dissolved in methylene chloride (1 mL), and the reaction was carried out at 60° C. for 2 hours. Following the reaction, the solvent was removed by evaporation. The product (Compound 10) was dissolved in methylene chloride (1 mL), 5-FU (21 mg) dissolved in pyridine (1 mL) was added, and the reaction was carried out at 0° C. for 30 minutes, then at room temperature for 12 hours. After the reaction, the solvent was removed by evaporation and purification was carried out with a reversed phase HPLC column (GL Sciences Inc.; Inertsil ODS-3, 20×50 mm; flow rate, 5 mL/min; developing solution, acetonitrile/water=20/80 (0 min) to 50/50 (30 min)), thereby giving Compounds 11 and 12 as a mixture. The yield was 45%.

ESI-MS [M+H]$^-$: theoretical value, 296.1; measured value, 296.1

Example 11

Evaluation of Cell Survival Rate (Low Oxygen Environment-Responsive 5-Fluorouracil)

Figure 7:
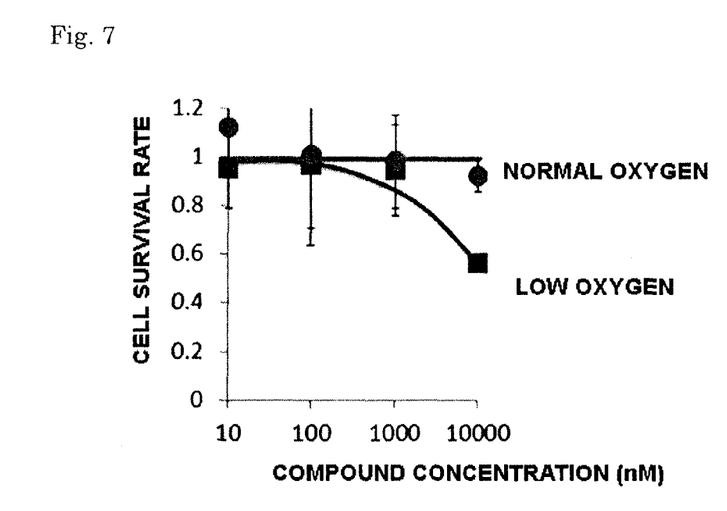
FIG. 7 is a graph showing the results of a cell survival rate evaluation (hypoxic environment-responsive 5-fluorourasil) in Example 11.

Human pancreatic cancer cells (MIA PaCa-2, acquired from Riken Cell Bank) were dispensed at a density of 5,000 cells/well and cultured for 24 hours in DMEM medium, following which a mixture of Compounds 11 and 12 was added to the specified concentration and 24 hours of culturing was carried out at a normal oxygen concentration (20%) or a low oxygen concentration (0.1%). After culturing, medium replacement was carried out, the compounds were removed, and 48 hours of culturing was carried out in a normal oxygen concentration incubator, following which the cell survival rate was analyzed by a WST assay. The results are shown in FIG. 7.

Example 12

Synthesis of Low Oxygen Environment-Responsive Mesalazine Prodrug

Reaction scheme:

[Chemical formula 12]

Compound 10 (0.11 mmol) synthesized in the same way as in Example 10 was dissolved in methylene chloride (1 mL), then mesalazine (16 mg) dissolved in pyridine (1 mL) was added and the reaction was carried out at 0° C. for 30 minutes, then at room temperature for 24 hours. After the reaction, the solvent was removed by evaporation, and purification was carried out with a reversed phase HPLC column (GL Sciences Inc.; Inertsil ODS-3, 20×50 mm; flow rate, 5 mL/min; developing solution, methanol/water=20/80 (0 min) to 20/80 (30 min)), thereby giving Compound 14. The yield was 35%.

ESI-MS [M−H]−: theoretical value, 319.07; measured value, 318.78

Example 13

Synthesis of Low Oxygen Environment-Responsive Melphalan Prodrug

Reaction scheme:

[Chemical formula 13]

Compound 10 (0.11 mmol) synthesized in the same way as in Example 10 was dissolved in methylene chloride (1 mL), then melphalan (32 mg) dissolved in pyridine (1 mL) was added and the reaction was carried out at 0° C. for 30 minutes, then at room temperature for 24 hours. After the reaction, the solvent was removed by evaporation and purification was carried out with a reversed phase HPLC column (GL Sciences Inc.; Inertsil ODS-3, 20×50 mm; flow rate, 5 mL/min; developing solution, methanol/water=20/80 (0 min) to 80/20 (30 min)), thereby giving Compound 15. The yield was 38%.

ESI-MS [M−H]−: theoretical value, 470.10; measured value, 469.63

Example 14

Synthesis of Low Oxygen Environment-Responsive Methotrexate Prodrug

Reaction scheme:

[Chemical formula 14]

16

17

Compound 10 (0.11 mmol) synthesized in the same way as in Example 10 was dissolved in methylene chloride (1 mL), then methotrexate (50 mg) dissolved in pyridine (1 mL) was added and the reaction was carried out at 0° C. for 30 minutes, then at room temperature for 24 hours. After the reaction, the solvent was removed by evaporation, and purification was carried out with a reversed phase HPLC column (GL Sciences Inc.; Inertsil ODS-3, 20×50 mm; flow rate, 5 mL/min; developing solution, methanol/water=20/80 (0 min) to 80/20 (30 min)), thereby giving a mixture of Compounds 16 and 17. The yield was 51%.

MALDI-TOF MS [M−H]⁻: theoretical value, 620.19; measured value, 620.38

Example 15

Synthesis of Low Oxygen Environment-Responsive Prednisolone Prodrug

Reaction scheme:

[Chemical formula 15]

-continued

13

Compound 10 (0.16 mmol) synthesized in the same way as in Example 10 was dissolved in methylene chloride (1 mL), then prednisolone (84 mg) dissolved in pyridine (1 mL) was added and the reaction was carried out at 0° C. for 30 minutes, then at room temperature for 24 hours. After the reaction, the solvent was removed by evaporation, partitioning between saturated saline and chloroform was carried out, and the organic phase was treated with sodium sulfate. The organic phase was then concentrated using an evaporator and purified by silica gel chromatography, giving Compound 13. The yield was 42%.

ESI-MS (M+H⁺): theoretical value, 528.23; measured value, 527.93

Example 16

Release of Drug from Prednisolone Prodrug in Low-Oxygen Environment

Human pancreatic cancer cells (MIA PaCa-2, acquired from Riken Cell Bank) were prepared as a suspension having a cell count of $1\times10^4$ cells/mL), and dispensed into a 96-well plate. After 24 hours, Compound 13 was added to a concentration of 10 and the cells were cultured in a normal oxygen concentration incubator (20% $O_2$) or at a low-oxygen work station (0.1% $O_2$). One hour layer, the culture medium was recovered, trypsin was added, and the cells were recovered. The recovered cells were disrupted by sonic treatment and the compound was extracted with acetonitrile, following which analysis by LC/MS of the amount of prednisolone released was carried out under the following conditions.

Column used: TSKgel ODS-100Z (particle size, 3 µm; 2 mm×75 mm) column
Measurement wavelength: 250 nm
Eluent A: 0.1 M ammonium acetate
Eluent B: acetonitrile
Flow rate: 0.2 mL/min
Gradient: 40:60 (Eluent A:Eluent B)→10:90 (20 minutes)

Figure 8:
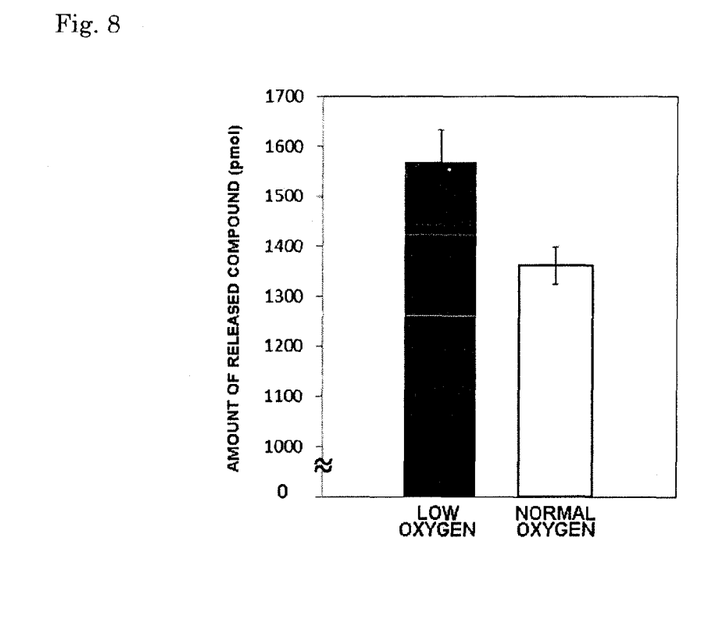
FIG. 8 is a graph showing the drug release behavior from a prednisolone prodrug within a hypoxic environment in Example 16.

By carrying out this measurement, the amount of compound released in a low-oxygen environment was compared with the amount released in a normal oxygen environment. The HPLC results are shown in FIG. 8. It is apparent from the diagram than much prednisolone is released in a low-oxygen environment.

INDUSTRIAL APPLICABILITY

This invention makes it possible to provide prodrugs which reduce the side effects of the parent compound in a normal oxygen concentration environment, but exhibit the activity inherent to the parent compound in a low-oxygen environment. This invention can be utilized in, for example, the pharmaceutical industry which provides therapeutically active organic compounds of reduced toxicity.

The invention claimed is:

1. A compound represented by general formula (I), (I)

wherein Z is of formula (a)

(a)

or of formula (b)

—O—R3     (b),

R1 being a residue of an amino group-bearing therapeutically active organic compound after removal of the amino group therefrom and R2 being a hydrogen atom, or R1 and R2, taken together with the adjoining nitrogen atom, being a residue of a therapeutically active organic compound having a cyclic amino group; and

R3 being a residue of a hydroxyl group-bearing therapeutically active organic compound after removal of the hydroxyl group therefrom, wherein the amino group-bearing therapeutically active organic compound is selected from the group consisting of doxorubicin and gemcitabine;
the therapeutically active organic compound having a cyclic amino group is represented by 5-fluorouracil;
the hydroxyl group-bearing therapeutically active organic compound is selected from the group consisting of doxorubicin and gemcitabine; and
the moiety corresponding to Z of general formula (I) is cleaved in a reducing environment, or a pharmaceutically acceptable salt thereof.

2. The compound according to claim 1 which has a formula as follows:

3. The compound according to claim 1 which has a formula as follows:

4. The compound according to claim 1 which has one of the following two formulae: